US011273300B2

(12) United States Patent
Schafir (10) Patent No.: US 11,273,300 B2
(45) Date of Patent: Mar. 15, 2022

(54) MAGNETICALLY SUSPENDED BLOOD DRIVING PISTON CIRCULATORY ASSIST DEVICE

(71) Applicant: HeartWare, Inc., Miami Lakes, FL (US)

(72) Inventor: David A. Schafir, Miami Shores, FL (US)

(73) Assignee: HEARTWARE, INC., Miami Lakes, FL (US)

(*) Notice: Subject to any disclaimer, the term of this patent is extended or adjusted under 35 U.S.C. 154(b) by 66 days.

(21) Appl. No.: 16/143,984

(22) Filed: Sep. 27, 2018

(65) Prior Publication Data

US 2019/0099533 A1    Apr. 4, 2019

Related U.S. Application Data

(60) Provisional application No. 62/567,887, filed on Oct. 4, 2017.

(51) Int. Cl.
*A61M 60/148* (2021.01)
*A61M 60/258* (2021.01)
(Continued)

(52) U.S. Cl.
CPC ........ *A61M 60/258* (2021.01); *A61M 60/148* (2021.01); *A61M 60/40* (2021.01);
(Continued)

(58) Field of Classification Search
CPC .............. A61M 1/1081; A61M 1/1055; A61M 1/1096; A61M 1/122; A61M 1/1087;
(Continued)

(56) References Cited

U.S. PATENT DOCUMENTS 3,791,769 A   2/1974  Kovacs
3,974,854 A   8/1976  Kurpanek
(Continued)

FOREIGN PATENT DOCUMENTS

WO    2017137486 A1    8/2017

OTHER PUBLICATIONS

International Search Report and Written Opinion dated Jan. 2, 2019, for corresponding International Application No. PCT/US2018/053089; International Filing Date: Sep. 27, 2018 consisting of 14-pages.

*Primary Examiner* — Paul B Prebilic
(74) *Attorney, Agent, or Firm* — Shumaker & Sieffert, P.A.

(57) ABSTRACT

A pulsatile blood pump including a chamber having an upstream portion, a downstream portion, and a wall coupling the upstream portion to the downstream portion, the upstream portion defining an inlet sized to fit within a ventricle of a heart, the downstream portion defining an outlet, and the wall defining a bore; a piston disposed within the bore of the wall, the piston including a first side in continuous fluid communication with the ventricle of the heart when the inlet is within the ventricle of the heart and defining a travel path within the bore including an upstream direction toward the inlet and a downstream direction toward the outlet; and a valve coupled to the piston and defining a one-way fluid flow path within the chamber through the first side of the piston in the downstream direction.

15 Claims, 4 Drawing Sheets

(51) Int. Cl.
*A61M 60/40* (2021.01)
*A61M 60/50* (2021.01)
*A61M 60/894* (2021.01)
*F04B 35/04* (2006.01)
*A61M 60/562* (2021.01)
*A61M 60/892* (2021.01)

(52) U.S. Cl.
CPC .......... *A61M 60/50* (2021.01); *A61M 60/894* (2021.01); *A61M 60/562* (2021.01); *A61M 60/892* (2021.01); *A61M 2205/3334* (2013.01); *F04B 35/045* (2013.01)

(58) Field of Classification Search
CPC .......... A61M 2205/04; A61M 2205/10; A61M 2205/3334; A61M 2205/3515; A61M 60/258; A61M 60/894; A61M 60/148; A61M 60/50; A61M 60/40; A61M 60/562; A61M 60/892
See application file for complete search history.

(56) References Cited

U.S. PATENT DOCUMENTS

| | | |
|---|---|---|
| 4,210,409 A | 7/1980 | Child |
| 4,610,658 A * | 9/1986 | Buchwald ........... A61M 27/002 417/417 |
| 5,108,426 A | 4/1992 | Biro et al. |
| 5,685,698 A | 11/1997 | Smoll |
| 5,693,091 A | 12/1997 | Larson, Jr. et al. |
| 5,722,930 A | 3/1998 | Larson, Jr. et al. |
| 5,924,975 A | 7/1999 | Goldowsky |
| 6,342,071 B1 | 1/2002 | Pless |
| 6,368,075 B1 * | 4/2002 | Fremerey ............ F04D 3/00 310/90.5 |
| 6,827,682 B2 | 12/2004 | Bugge et al. |
| 7,303,581 B2 | 12/2007 | Peralta |
| 8,167,593 B2 | 5/2012 | Gohean et al. |
| 8,366,401 B2 | 2/2013 | Pate et al. |
| 8,386,040 B2 | 2/2013 | Pate et al. |
| 8,568,113 B2 | 10/2013 | Pate et al. |
| 9,492,601 B2 | 11/2016 | Casas et al. |
| 2003/0032853 A1 | 2/2003 | Korakianitis et al. |
| 2006/0030746 A1 | 2/2006 | Grossmann |
| 2010/0266422 A1 | 10/2010 | Pate et al. |
| 2010/0266423 A1 | 10/2010 | Gohean et al. |
| 2010/0268333 A1 | 10/2010 | Gohean et al. |
| 2010/0268334 A1 | 10/2010 | Pate et al. |
| 2013/0330219 A1 * | 12/2013 | LaRose ............ F04D 29/041 417/420 |
| 2014/0058190 A1 | 2/2014 | Gohean et al. |
| 2015/0038772 A1 | 2/2015 | Heilman et al. |
| 2017/0224894 A1 | 8/2017 | Najar |
| 2018/0085505 A1 * | 3/2018 | Casas ............... A61M 1/101 |

* cited by examiner

MAGNETICALLY SUSPENDED BLOOD DRIVING PISTON CIRCULATORY ASSIST DEVICE

CROSS-REFERENCE TO RELATED APPLICATION

This application claims the benefit of U.S. application Ser. No. 62/567,887, filed Oct. 4, 2017, the entirety of which is incorporated herein by reference.

FIELD

The present technology generally relates to a mechanical circulatory assist device.

BACKGROUND

Mechanical circulatory assist devices, such as implantable blood pumps, provide mechanical circulatory support to patients having a weakened or otherwise compromised heart. Generally, implantable blood pumps include a pumping mechanism to move blood from the heart to the rest of the body by pulsatile motion or by continuous flow. Pulsatile blood pumps are configured to pump blood in a manner similar to a heart. Piston pumps are one example of a pulsatile blood pump. Piston pumps are positive displacement pumps typically used to move fluid, such as water. Piston pumps include a piston which draws water through an inlet valve during an upstroke into a cylindrical chamber inside the pump. During a downstroke, the fluid is discharged through an outlet valve.

Pulsatile blood pumps, such as the piston pumps, may allow for the aortic valve to open, which is not inherently possible with continuous flow pumps without employing speed reduction schemes to temper the flow of the blood. However, pulsatile blood pumps may include numerous mechanical components that can undergo wear and tear over time which negatively affects the pumping function of the device. As a result, continuous flow pumps may be preferred over pulsatile blood pumps for this reason. Nevertheless, continuous flow pumps may cause gastrointestinal bleeding due to a lack of pulsatility.

SUMMARY

The techniques of this disclosure generally relate to a pulsatile blood pump.

In one aspect, the present disclosure provides a pulsatile blood pump including a chamber including an upstream portion, a downstream portion, and a wall coupling the upstream portion to the downstream portion, the upstream portion defining an inlet sized to fit within a ventricle of a heart, the downstream portion defining an outlet, and the wall defining a bore; a piston disposed within the bore of the wall, the piston including a first side in continuous fluid communication with the ventricle of the heart when the inlet is within the ventricle of the heart and defining a travel path within the bore including an upstream direction toward the inlet and a downstream direction toward the outlet; and a valve coupled to the piston and defining a one-way fluid flow path within the chamber through the first side of the piston in the downstream direction.

In another aspect, the disclosure provides the piston including a second side opposite the first side, the second side having the valve coupled thereto.

In another aspect, the disclosure provides the piston defining an aperture extending between the first side and the second side of the piston.

In another aspect, the disclosure provides the pulsatile blood pump having a filling stage including the piston traveling in the upstream direction toward the inlet, and the valve being in an open configuration.

In another aspect, the disclosure provides the pulsatile blood pump having a pumping stage including the piston traveling in the downstream direction toward the outlet, and the valve being in a closed configuration.

In another aspect, the disclosure provides the piston including a second side opposite the first side, the second side having the valve coupled thereto.

In another aspect, the disclosure provides one or more stator coils coupled to the chamber, and wherein the piston includes one or more magnets in communication with the stator coils.

In another aspect, the disclosure provides the stator coils hermetically sealed within the wall of the chamber.

In another aspect, the disclosure provides the piston defining a wall including the magnets hermetically sealed therein.

In another aspect, the disclosure provides the inlet being sized to fit within the ventricle of the heart at an apex of the heart.

In another aspect, the disclosure provides the piston and the wall of the chamber defining a gap therebetween.

In another aspect, the present disclosure provides a pulsatile blood pump including a magnetically suspended piston disposed within the chamber, the piston including a first side in continuous fluid communication with the ventricle of the heart when the inlet is within the ventricle of the heart and defining a travel path within the chamber between the inlet and the outlet of the chamber; and a valve coupled to the piston, the valve having an open configuration including the valve defining a fluid flow path within the chamber from the inlet to the outlet and a closed configuration including the valve obstructing a fluid from traveling from the outlet toward the inlet.

In another aspect, the disclosure provides the piston including a second side opposite the first side, and the valve is coupled to the second side of the piston.

In another aspect, the disclosure provides the piston defining an aperture and the fluid flow path is through the aperture and the valve.

In another aspect, the disclosure provides the valve being a one-way valve and the fluid flow path being a one-way fluid flow path from the inlet to the outlet through the valve.

In another aspect, the disclosure provides a valve coupled to the piston and defining a one-way fluid flow path within the chamber.

In another aspect, the disclosure provides one or more stator coils coupled to the chamber, and one or more magnets coupled to the piston, the plurality of magnets being in communication with the plurality of stator coils.

In another aspect, the disclosure provides the chamber and the piston each defining a wall, the wall of the chamber including the stator coils hermetically sealed therein and the wall of the piston including the plurality of magnets hermetically sealed therein.

In another aspect, the disclosure provides the piston and the wall of the chamber defining a gap therebetween.

In another aspect, the disclosure provides the stator coils and the magnets defining an alternating magnetic field for cyclical movement of the piston within the chamber.

In another aspect, the disclosure provides the cyclical movement of the piston being synchronized with a cardiac cycle of the heart.

In another aspect, the present disclosure provides a pulsatile blood pump including a chamber having an upstream portion, a downstream portion, and a wall coupling the upstream portion to the downstream portion, the upstream portion defining an inlet sized to fit within a ventricle of a heart, the downstream portion defining an outlet, and the wall defining a bore; a piston disposed within the bore of the wall and defining a travel path including an upstream direction toward the inlet and a downstream direction toward the outlet, the piston including a first side, a second side opposite the first side, and a wall coupling the first side and the second side of the piston to each other, the first side being in continuous fluid communication with the ventricle of the heart when the inlet is within the ventricle of the heart; a valve coupled to the second side of the piston and defining a one-way fluid flow path within the chamber in the downstream direction toward the outlet; one or more stator coils hermetically sealed within the wall of the chamber; and one or more magnets hermetically sealed within the wall of the piston.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Before describing in detail exemplary embodiments, it is noted that the embodiments reside primarily in combinations of device and method components related to a magnetically suspended blood driving piston circulatory assist device. Accordingly, the device and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Referring now to the drawings in which like reference designators refer to like elements, there is shown in FIGS. 1-5 an exemplary pulsatile blood pump constructed in accordance with the principles of the present application and designated generally as "10." The blood pump 10 is a type of mechanical circulatory assist device including a piston which moves in a cyclical motion forcing blood to travel in a single direction from an inlet to an outlet of the blood pump 10. The piston includes a single valve coupled thereto such that the blood pump 10 may be in continuous fluid communication with a ventricle of a heart.

Figure 1:
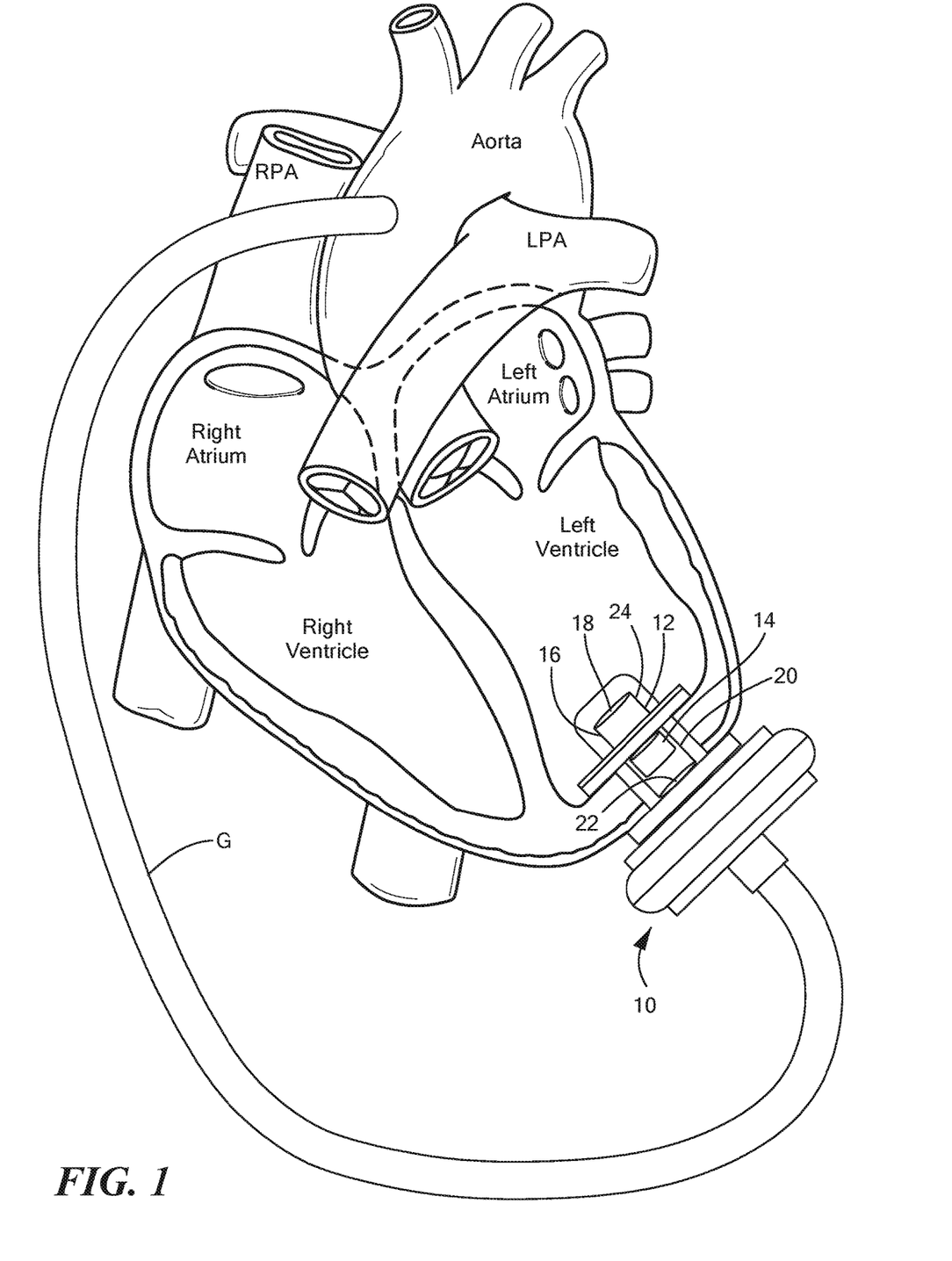
FIG. 1 is a perspective view of a pulsatile blood pump that illustrates the pulsatile blood pump coupled to a heart.

FIG. 1 depicts the blood pump 10 implanted into a left ventricle at an apex of a mammalian heart of a patient, although other locations of the heart are contemplated. The blood pump 10 includes an outer housing for housing a chamber 12 and a piston 14 disposed within the chamber 12. The outer housing may be of various configurations, for example, that which is sold under the designation HVAD®. The chamber 12 includes an upstream portion 16 defining an inlet 18 sized to fit within the heart and a downstream portion 20 defining an outlet 22 opposite the inlet 18. The upstream portion 16 and the downstream portion 20 are coupled to each other through a wall 24 of the chamber 12. The blood pump 10 may be implanted using a sewing ring or other coupling device such that, upon implantation, the inlet 18 is located within the heart and the outlet 22 is connected to an external graft "G" configured to transport blood from the heart to an aorta of the patient.

Figure 2:
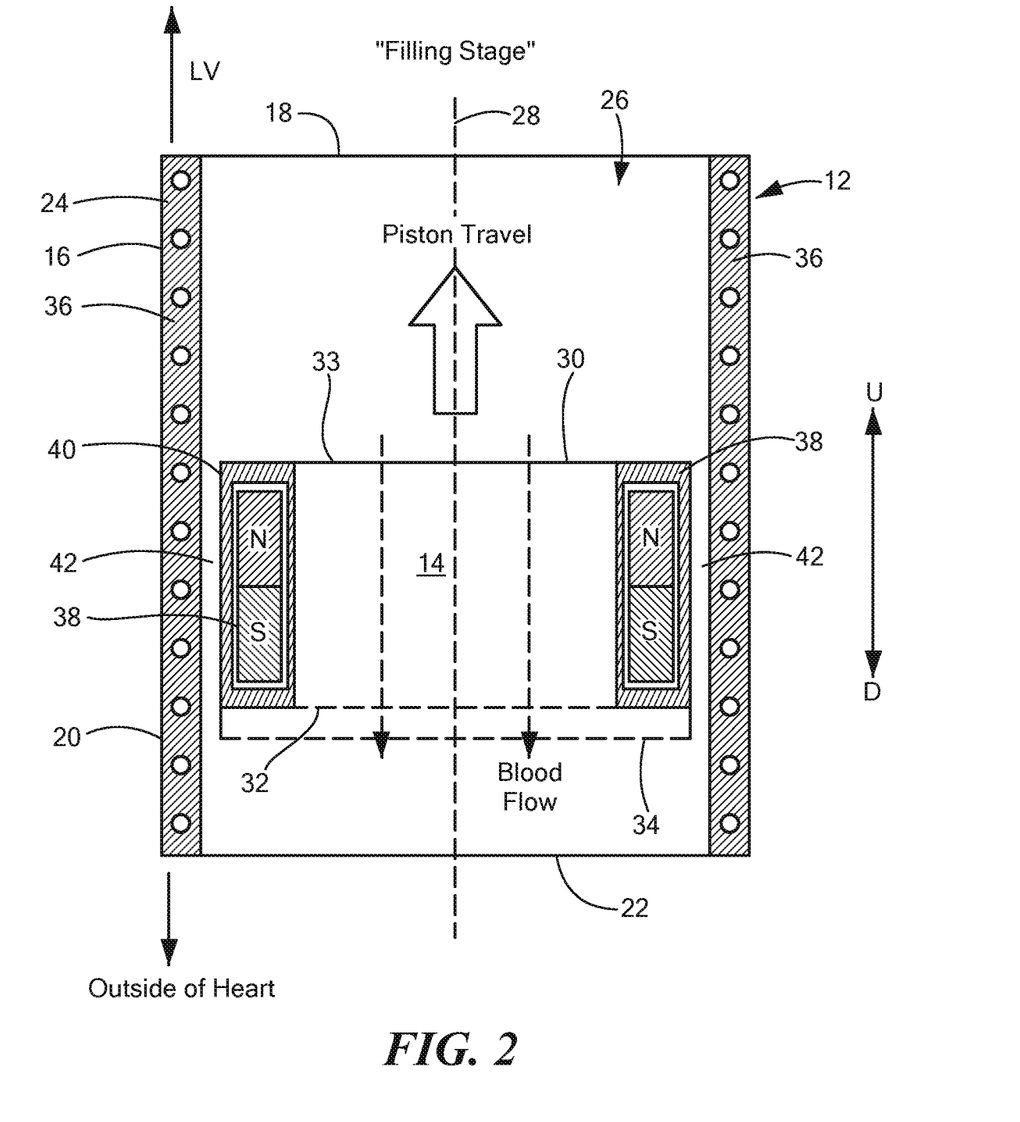
FIG. 2 is a sectional side view of a chamber of the pulsatile blood pump of FIG. 1 that illustrates the pulsatile blood pump during a filling stage.

FIG. 2 depicts the wall 24 of the chamber 12 being cylindrical and defining a bore 26 for receiving the piston 14 therein. The cylindrical shape of the wall 24 is not intended to be limiting as the chamber 12 may be provided in various shapes. The chamber 12 defines a longitudinal axis 28 extending from the upstream portion 16 through the downstream portion 20 of the chamber 12. The piston 14 defines a travel path within the chamber 12 along the longitudinal axis 28 between an upstream direction "U" and a downstream direction "D" to create a pulsatile motion of the blood pump 10. The upstream direction is toward the upstream portion 16 and the inlet 18 of the chamber 12, whereas the downstream direction is toward the downstream portion 20 and the outlet 22 of the chamber 12. In other words, the piston 14 moves in a cyclical motion within the chamber 12 between the upstream portion 16 and the downstream portion 20 to cause a fluid, such as blood, to travel from the inlet 18 to the outlet 22 of the chamber 12.

Figure 3:
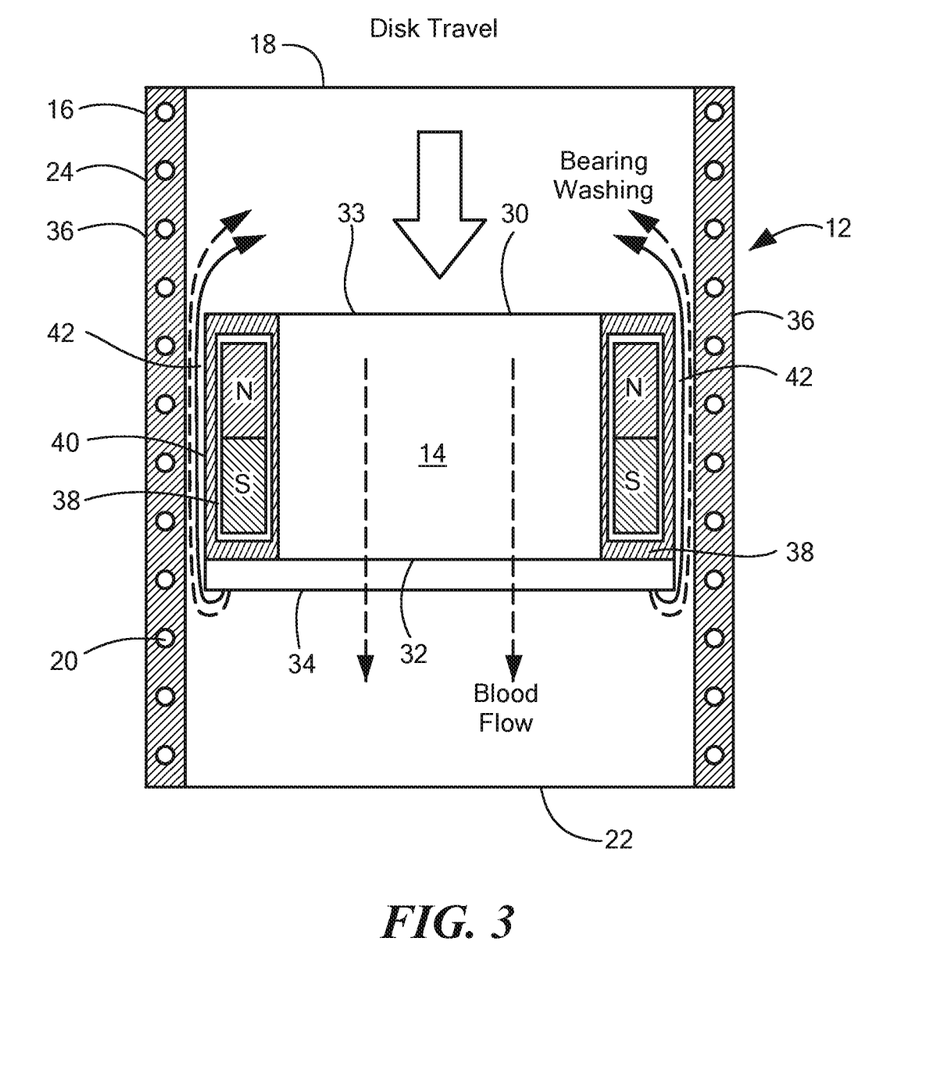
FIG. 3 is a sectional side view of the chamber of the pulsatile blood pump of FIG. 1 that illustrates the pulsatile blood pump during a pumping stage.

FIGS. 2 and 3 depict the piston 14 including a first side 30 facing toward the inlet 18 and a second side 32 facing toward the outlet 22 of the chamber 12. As such, the second side 32 of the piston 14 is opposite the first side 30. The first side 30 of the piston 14 defines an aperture 33 from the first side 30 of the piston 14 to the second side 32 of the piston 14. Accordingly, when the blood pump 10 is coupled to the heart, the inlet 18 and the first side 30 of the piston 14 are in continuous communication with the ventricle of the heart as there are no intervening structures, such as valves, between the first side 30 of the piston 14 and the heart. In other words, blood from the ventricle of the heart flows freely through the inlet 18 into the first side 30 of the piston 14 and the aperture 33 without any obstructions.

When the blood pump 10 is implanted and operational, the piston 14 moves in the cyclical motion within the chamber 12 so as to mimic the pumping action of the heart. The cyclical movement of the piston 14 is performed while maintaining the continuous communication between the chamber 12 and the ventricle through the inlet 18. The cyclical movement may include two cycles, wherein each cycle consists of a first stoke and a second stroke that may be synchronized with a cardiac cycle of the heart.

For example, FIG. 2 depicts the first stroke of the cyclical motion in which the blood pump 10 is in a filling stage including the piston 14 moving in the upstream direction towards the inlet 18 against the normal flow of blood from the ventricle. During this stroke, a valve 34 coupled to the second side 32 of the piston 14 opens under the pressure of the incoming blood flow and allows the blood to flow in the downstream direction generating a pulsatile cycle of blood flow through the blood pump 10. In other words, in the filling stage, the valve 34 is in an open configuration and defines a one-way fluid flow path through the first side 30 of the piston 14 from the upstream portion 16 to the downstream portion 20 of the chamber 12. The one-way flow path is an uninhibited flow path and the open configuration of the valve 34 is indicated by the dashed lines. In one configuration, the valve 34 is the only valve of the blood pump 10 and may be a check valve or another type of one-way valve 34.

FIG. 3 depicts the second stroke of the cyclical motion in which the blood pump 10 is in a pumping stage including the piston 14, upon reaching the upstream portion 16 of the chamber 12, reversing and moving in the downstream direction, with the normal flow of blood. During the second stroke, the valve 34 closes and prevents any flow of blood through the piston 14 in the upstream direction. FIG. 3 depicts the dashed lines of the valve 34 converted to a solid line representing the valve 34 being closed in a closed configuration. The downstream movement of the piston 14 forces blood in the downstream direction towards the outlet 22 and into the graft when the graft is connected to the blood pump 10 at an apex of the heart. In one embodiment, unlike continuous flow blood pumps, the cyclical motion of the blood pump 10 may be configured to force an aortic valve of the heart to open. For example, movement of the piston 14 in the upstream direction pushes blood through the inlet 18 of the blood pump 10 into the aortic valve and thereafter into the aorta. The outlet 22 of the chamber 12 is configured to be in communication with an artery, such as the aorta.

The blood pump 10 provides minimal components for operation in a relatively simple manner and which are subject to nominal wear and tear. For example, FIGS. 2 and 3 depict the piston 14 magnetically suspended within the chamber 12 using one or more stator coils 36 which may be part of a stator and which are hermetically sealed within the wall 24 of the chamber 12. The stator coils 36 communicate with a power source and a control circuit (not shown) to produce an alternating magnetic field formed by changing a current intensity and a direction within the stator coils 36 and may operate similar to that of a solenoid switch. The power source may be internal or external, such as a battery, an electrical power source, a mains power connection, or the like. The control circuit may also monitor and control further operations of the blood pump 10 implemented at least in part by a general-purpose processor, a memory, data, instructions, and an interface. Further details of an exemplary control circuit, general-purpose processor, memory, data, instructions, and interface may be found in U.S. Pat. No. 9,492,601B2, the disclosure of which is incorporated herein in the entirety.

The piston 14 includes one or more magnets 38 or ferromagnetic members in communication with the alternating magnetic field of the stator coils 36 to adjust an axial position and/or a radial position of the piston 14 within the chamber 12. The axial position includes the cyclic movement between the upstream portion 16 and the downstream portion 20 of the chamber 12. The magnets 38 include a ferromagnetic material and may be permanent magnets, full-ring permanent magnets, or the like, hermetically sealed around and within a wall 40 of the piston 14.

The wall 24 of the chamber 12 and the wall 40 of the piston 14 define a gap 42 therebetween which allows a backwashing of the blood through the gap 42. As the piston 14 moves from the upstream direction to the downstream direction, the blood may travel through the gap 42 from the downstream direction to the upstream direction opposite the piston 14. The blood flowing through and around the piston 14 washes the piston 14 to reduce the risk of thrombus formation by preventing the blood from becoming stagnant as a result of possible friction between the blood and the wall 40 of the piston 14. The gap 42 may be maintained between the piston 14 and the wall 24 of the chamber 12 during the cyclical motion of the piston 14 when the piston 14 is driven by the alternating magnetic field and magnetically suspended within the chamber 12.

Figure 4:
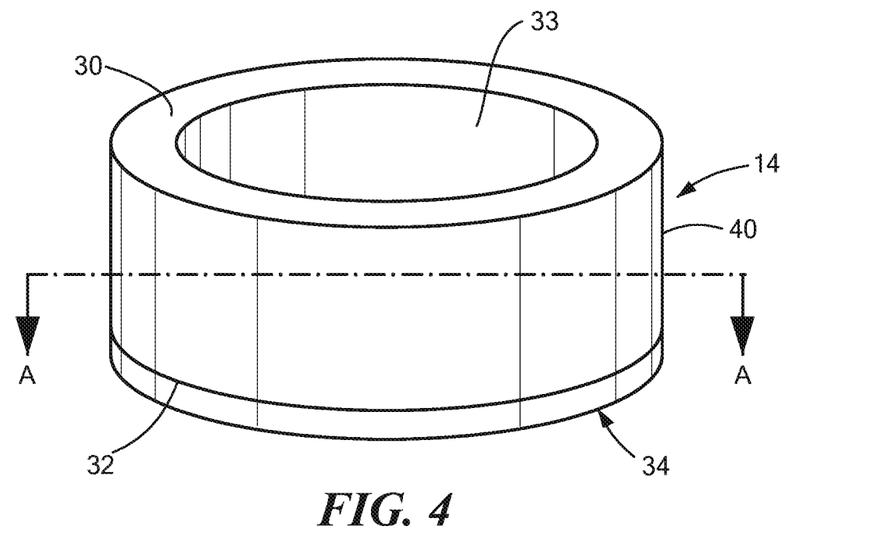
FIG. 4 a front perspective view of a valve and a piston of the pulsatile blood pump of FIG. 1.
Figure 5:
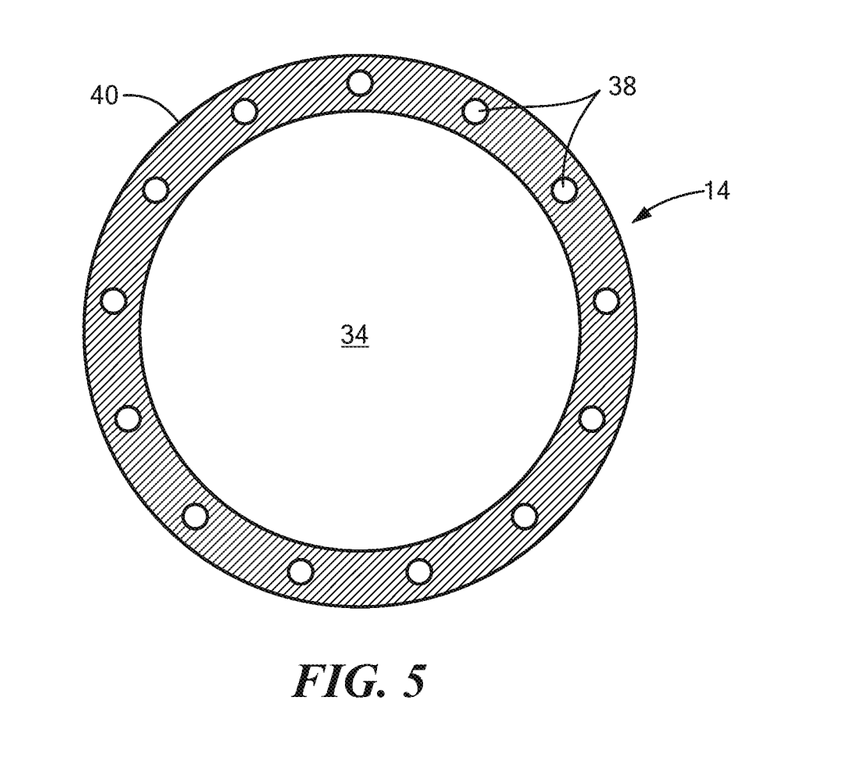
FIG. 5 is a sectional top plan view of the piston of FIG. 4 taken along section AA.

FIG. 4 depicts the valve 34 in the closed configuration in which the valve 34 is closed and thus obstructing the fluid from flowing from the outlet 22 toward the inlet 18 of the chamber 12. In addition, the valve 34 is coupled to the second side 32 of the piston 14 opposite the first side 30 of the piston 14. FIG. 5 depicts a sectional top plan view of the piston 14 taken along section A-A of FIG. 4. The wall 40 of the piston 14 surrounds the valve 34 and the magnets 38 are hermetically sealed within the wall 40.

It will be appreciated by persons skilled in the art that the present disclosure is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the disclosure, which is limited only by the following claims.

What is claimed is:

1. A pulsatile blood pump comprising:
    a housing, the housing including:
        a chamber defined within the housing and including an upstream portion, a downstream portion, and a wall coupling the upstream portion to the downstream portion, the upstream portion defining an inlet sized to fit within a ventricle of a heart, the downstream portion defining an outlet, and the wall defining a bore;
        a piston disposed within the bore of the wall, the piston including a first side and a second side opposite the first side, the first side being in continuous fluid communication with the ventricle of the heart when the inlet is within the ventricle of the heart and defining a travel path within the bore including an upstream direction toward the inlet and a downstream direction toward the outlet, the piston further defining an aperture extending between the first side and the second side of the piston, the second side including a first face facing the upstream end and a second face facing the downstream end;
        a valve integrated with and downstream to the second face of the second side of the piston and defining a one-way fluid flow path within the chamber in the downstream direction toward the outlet; and
        a plurality of magnets hermetically sealed within the wall of the piston and perpendicular to the second side, the plurality of magnets being circumferentially spaced apart from each other around a circumference of the piston.

2. The pulsatile blood pump of claim 1, wherein the chamber defines a longitudinal axis extending from the upstream portion through the downstream portion, the piston and the plurality of magnets being entirely movable along the longitudinal axis in the upstream direction toward the inlet when the valve is in an open configuration.

3. The pulsatile blood pump of claim 2, wherein the piston travels in the downstream direction toward the outlet when the valve is in a closed configuration.

4. The pulsatile blood pump of claim 1, further comprising a plurality of stator coils coupled to the chamber, and wherein the plurality of magnets are in communication with the plurality of stator coils.

5. The pulsatile blood pump of claim 4, wherein the plurality of stator coils are hermetically sealed within the wall of the chamber.

6. The pulsatile blood pump of claim 1, wherein the inlet is sized to fit within the ventricle of the heart at an apex of the heart.

7. The pulsatile blood pump of claim 1, wherein the piston and the wall of the chamber define a gap therebetween.

8. A pulsatile blood pump comprising:
    a housing, the housing including:
        a chamber defined within the housing and including an upstream portion, a downstream portion, and a longitudinal axis defined from the upstream portion through the downstream portion, the chamber defining an inlet sized to fit within a ventricle of a heart and an outlet opposite the inlet;
        a magnetically suspended piston disposed within the chamber, the piston including a first side and a second side opposite the first side, the first side being in continuous fluid communication with the ventricle of the heart when the inlet is within the ventricle of the heart and defining a travel path within the chamber between the inlet and the outlet of the chamber, the first side including a first face facing the upstream portion and the second side including a second face facing the downstream portion;
        a check valve integrated with and downstream from the second face of the second side of the piston, the valve having an open configuration including the valve defining a fluid flow path within the chamber in a downstream direction from the inlet to the outlet and a closed configuration including the valve obstructing a fluid from traveling from the outlet toward the inlet, the piston further defining an aperture and the fluid flow path being through the aperture and the valve;
        a plurality of magnets hermetically sealed within a wall of the piston and perpendicular to the second side, the plurality of magnets being circumferentially spaced apart from each other around a circumference of the piston; and
        the piston and the plurality of magnets being entirely movable along the longitudinal axis between the upstream portion and the downstream portion.

9. The pulsatile blood pump of claim 8, wherein the valve is a one-way valve and the fluid flow path is a one-way fluid flow path from the inlet to the outlet through the valve.

10. The pulsatile blood pump of claim 8, further comprising a plurality of stator coils coupled to the chamber, the plurality of magnets being in communication with the plurality of stator coils.

11. The pulsatile blood pump of claim 10, wherein the chamber defines a wall, the wall of the chamber including the plurality of stator coils hermetically sealed.

12. The pulsatile blood pump of claim 11, wherein the piston and the wall of the chamber define a gap therebetween.

13. The pulsatile blood pump of claim 11, wherein the plurality of stator coils and the plurality of magnets define an alternating magnetic field for cyclical movement of the piston within the chamber.

14. The pulsatile blood pump of claim 13, wherein the cyclical movement of the piston is synchronized with a cardiac cycle of the heart.

15. A pulsatile blood pump comprising:
a housing, the housing including:
  a chamber defined within the housing and including an upstream portion, a downstream portion, a longitudinal axis extending from the upstream portion through the downstream portion, and a wall coupling the upstream portion to the downstream portion, the upstream portion defining an inlet sized to fit within a ventricle of a heart, the downstream portion defining an outlet, and the wall defining a bore;
  a piston disposed within the bore of the wall and defining a travel path including an upstream direction toward the inlet and a downstream direction toward the outlet, the piston including a first side, a second side opposite the first side, and a wall coupling the first side and the second side of the piston to each other, the first side being in continuous fluid communication with the ventricle of the heart when the inlet is within the ventricle of the heart, the piston further defining an aperture extending between the first side and the second side of the piston, the first side including a first face facing the upstream portion and the second side including a second face facing the downstream portion;
a check valve integrated with and downstream to the second face of the second side of the piston and defining a one-way fluid flow path within the chamber in the downstream direction toward the outlet;
a plurality of stator coils hermetically sealed within the wall of the chamber;
a plurality of magnets hermetically sealed within the wall of the piston and perpendicular to the second side, the plurality of magnets being circumferentially spaced apart from each other around a circumference of the piston; and
the piston and the plurality of magnets being entirely movable along the longitudinal axis between the upstream portion and the downstream portion.

* * * * *